(12) United States Patent
Sang

(10) Patent No.: US 8,309,570 B2
(45) Date of Patent: Nov. 13, 2012

(54) TREATMENT OF CENTRAL NEUROPATHIC PAIN

(75) Inventor: Christine Nai-Mei Sang, Brookline, MA (US)

(73) Assignee: Analgesic Neuropharmaceuticals, LLC, Brookline, MA (US)

( * ) Notice: Subject to any disclaimer, the term of this patent is extended or adjusted under 35 U.S.C. 154(b) by 1525 days.

(21) Appl. No.: 10/477,881

(22) PCT Filed: Jun. 7, 2001

(86) PCT No.: PCT/US01/18723
§ 371 (c)(1),
(2), (4) Date: Aug. 23, 2004

(87) PCT Pub. No.: WO02/100434
PCT Pub. Date: Dec. 19, 2002

(65) Prior Publication Data
US 2005/0009916 A1 Jan. 13, 2005

Related U.S. Application Data

(60) Provisional application No. 60/297,145, filed on Jun. 7, 2001.

(51) Int. Cl.
*A61K 31/44* (2006.01)
*A61K 31/195* (2006.01)

(52) U.S. Cl. ........................ 514/289; 514/567

(58) Field of Classification Search .................. 514/662, 514/566
See application file for complete search history.

(56) References Cited

U.S. PATENT DOCUMENTS

| | | | |
|---|---|---|---|
| 4,316,888 A | 2/1982 | Nelson | |
| 4,446,140 A | 5/1984 | Nelson | |
| 5,164,398 A | 11/1992 | Sims et al. | |
| 5,352,683 A | 10/1994 | Mayer et al. | |
| 5,502,058 A * | 3/1996 | Mayer et al. | 514/289 |
| 5,834,479 A | 11/1998 | Mayer et al. | |
| 5,840,731 A | 11/1998 | Mayer et al. | |
| 5,863,922 A | 1/1999 | Mayer et al. | |
| 5,863,927 A | 1/1999 | Smith et al. | |
| 5,869,498 A | 2/1999 | Mayer et al. | |
| 5,891,885 A | 4/1999 | Caruso | |
| 5,919,826 A | 7/1999 | Caruso | |
| 5,925,634 A | 7/1999 | Olney | |
| 6,007,841 A | 12/1999 | Caruso | |
| 6,015,797 A | 1/2000 | Camborde et al. | |
| 6,054,451 A | 4/2000 | Caruso | |
| 6,187,338 B1 | 2/2001 | Caruso et al. | |
| 6,194,000 B1 | 2/2001 | Smith et al. | |
| 6,406,716 B2 | 6/2002 | Caruso et al. | |
| 6,649,605 B2 | 11/2003 | Olesen et al. | |
| 6,825,203 B2 | 11/2004 | Pasternak et al. | |
| 7,256,200 B2 | 8/2007 | Wang | |
| 2001/0036943 A1 | 11/2001 | Coe et al. | |
| 2002/0035105 A1 | 3/2002 | Caruso | |
| 2003/0100507 A1 | 5/2003 | Gulati | |
| 2005/0009916 A1 | 1/2005 | Sang | |
| 2005/0038062 A1 | 2/2005 | Burns et al. | |
| 2005/0226930 A1 | 10/2005 | Krsek et al. | |
| 2006/0052370 A1 | 3/2006 | Meyerson et al. | |
| 2006/0094741 A1 | 5/2006 | Nagase et al. | |
| 2006/0167032 A1 | 7/2006 | Galer et al. | |
| 2006/0178354 A1 | 8/2006 | Lucas | |
| 2006/0199841 A1 | 9/2006 | Tihanyi et al. | |
| 2006/0240043 A1 | 10/2006 | Meyerson et al. | |
| 2006/0240128 A1 | 10/2006 | Schlagheck | |

FOREIGN PATENT DOCUMENTS

| | | |
|---|---|---|
| CA | 2264182 | 2/1998 |
| CA | 2289190 | 11/1998 |
| CA | 2359485 | 9/2000 |
| EP | 0 615 749 A2 | 9/1994 |
| EP | 0615749 | 9/1994 |
| EP | 1 205 187 A1 | 5/2002 |
| WO | WO-9714415 | 1/1997 |
| WO | WO-9807447 | 2/1998 |
| WO | WO 98/50044 | 11/1998 |
| WO | WO-9850044 | 11/1998 |
| WO | WO-9850075 | 11/1998 |
| WO | WO 99/08669 A1 | 2/1999 |
| WO | WO-9907413 | 2/1999 |
| WO | WO-9945963 | 9/1999 |
| WO | WO-0003716 | 1/2000 |
| WO | WO-0029023 | 5/2000 |
| WO | WO 00/44371 A1 | 8/2000 |

(Continued)

OTHER PUBLICATIONS

Sang, C. N., "NMDA-Receptor Antagonists in Neuropathic Pain: Experimental Methods to Clinical Trials", Journal of Pain and Symptom Management, vol. 19 No. 1 (Suppl.) Jan. 2000, pp. S21-S25.*

(Continued)

*Primary Examiner* — Sreeni Padmanabhan
*Assistant Examiner* — Jody Karol
(74) *Attorney, Agent, or Firm* — Choate, Hall & Stewart LLP; Brenda Herschbach Jarrell; Danielle M. Nihan

(57) ABSTRACT

Central neuropathic pain is treated with an analgesic composition that consists essentially of an N-methyl-D-aspartate (NMDA) receptor antagonist. In one embodiment, the invention includes chronic administration of the (NMDA) receptor antagonist. In another embodiment, the invention is use of an NMDA receptor antagonist or component thereof for the manufacture of a medicament than includes an analgesic component that consists essentially of an NMDA receptor antagonist for the chronic treatment of central neuropathic pain.

16 Claims, 6 Drawing Sheets

FOREIGN PATENT DOCUMENTS

| WO | WO 01/05963 A2 | 1/2001 |
|---|---|---|
| WO | WO 01/08705 A1 | 2/2001 |
| WO | WO-0361656 | 7/2003 |
| WO | WO-2005102390 | 11/2005 |

OTHER PUBLICATIONS

Geter-Douglas et al., "Behavioral Effects and Anticonvulsant Efficacies of Low-Affinity, Uncompetitive NMDA Antagonists in Mice", Psychopharmacology (1999) 146:280-289.*
Mao et al., "Gabapentin in Pain Management", Anest. Analg. 2000; 91:680-7.*
Hao et al., "Repeated administration of systemic gabapentin alleviates allodynia-like behaviors in spinally injured rats," Neuroscience Letters, 280 (2000), pp. 211-214.*
Suzuki, et al.; "Comparison of the effects of MK-801, ketamine and memantine on responses of spinal dorsal horn neurones in a rat model of mononeuropathy"; Pain (2001); vol. 91, No. 1/2, pp. 101-109.
Hao, Jing-Xia, et al.; "Treatment of a chronic allodynia-like response in spinally injured rats: effects of systemically administered excitatory amino acid receptor antagonists"; Pain; (1996); vol. 66, No. 203, pp. 279-285.
Chizh, et al.; "Supraspinal vs spinal sites of the antinociceptive action of the subtype-selective NMDA antagonist ifenprodil"; Neuropharmacology; (2001); vol. 40, pp. 212-220.
Ben-Abraham et al., "Dextromethorphan in Chronic Pain: A Disappointing Update," IMAJ, 2000, pp. 708-710, 2.
Canadian Monograph, Drug Monograph for Amantadine (Symmetrel), pp. 1-8, last retrieved Aug. 14, 2008.
Carlton et al., "Dextrorphan Attenuates Responses of Spinothalamic Tract Cells in Normal and Nerve-injured Monkeys," Neuroscience Letters, 1997, pp. 169-172, 229(3).
Chaplan et al., "Efficacy of Spinal NMDA Receptor Antagonism in Formalin Hyperalgesia and Nerve Injury Evoked Allodynia in the Rat," Journal of Pharmacology and Experimental Therapeutics, 1997, pp. 829-838, 280(2).
Chizh et al., "Supraspinal vs Spinal Sites of the Antinociceptive Action of the Subtype-selective NMDA Antagonist Ifenprodil," Neuropharmacology, 2001, pp. 212-220, 40(2), ISSN: 0028-3908.
Devor et al., American Pain Society Abstract, No. 321, "New Drug Treatments for Neuropathic Pain: A Critical Look at Recent Clinical Trials of Blockers of Excitatory Amino Acids Receptors or Sodium Channels," 1997, pp. 68.
Elliott, et al., "N-Methyl-D-Aspartate (NMDA) Receptors, Mu and Kappa Opioid Tolerance, and Perspectives on New Analgesic Drug Development," Neuropsychopharmacology, 1995, pp. 347-356, 13(4).
Geter-Douglass et al., "Behavioral Effects and Anticonvulsant Efficacies of Low-Affinity, Uncompetitive NMDA Antagonists in Mice," Psychopharmacology, 1999, pp. 280-289, 146.
Gilron et al., "A Randomized, Controlled Trial of High-dose Dextromethorphan in Facial Neuralgias," Neurology, 2000, pp. 964-971, 55(7).
Glick et al., "Antagonism of α3β4 Nicotinic Receptors as a Strategy to Reduce Opioid and Stimulant Self-Administration," European Journal of Pharmacology, 2002, pp. 99-105, 438.
Grant et al., "Dizocilpine-like Discriminative Stimulus Effects of Low-Affinity Uncompetitive NMDA Antagonists," Neuropharmacology, 1996, pp. 1709-1719, 35.
Hao et al., "Treatment of a Chronic Allodynia-like Response in Spinally Injured Rats: Effects of Systemically Administered Excitatory Amino Acid Receptor Antagonists," Pain, 1996, pp. 279-285, 66(2-3), ISSN: 0304-3959.
Hubscher et al., "Chronic Spinal Cord Injury Induced Changes in the Responses of Thalamic Neurons," Experimental Neurology, 2006, pp. 177-188, 197.
International Application No. PCT/US01/018723 PCT International Search Report.
Kauppila et al., "Dextromethorphan Potentiates the Effect of Morphine in Rats with Peripheral Neuropathy," NeuroReport, 1998, pp. 1071-1074, 9(6).
Long et al., "Selective δ Ligands Protect Against Spinal Cord Injury in Rats: In Vivo and In Vitro Evidence," Neuromodulation Neuroprot. Proc. Jt. Fr.-U.S. Semin, CNRS-NSF, 1992, 3, Meeting Date 1991, pp. 673-686.
Mao et al., "Gabapentin in Pain Management," Anesth Analg, 2000, pp. 680-687, 91.
Mayo Foundation for Medical Education and Research, Micromedex Drug Information for Dextromethorphan (Oral Route), pp. 1-5, last retrieved Aug. 13, 2009.
McCartney et al., "A Qualitative Systematic Review of the Role of N-Mehtyl-D-Aspartate Receptor Antagonists in Preventive Analgesia," Anesth Analg, 2004, pp. 1385-1400, 98.
McQuay et al., "Dextromethorphan for the Treatment of Neuropathic Pain: A Double-blind Randomized Controlled Crossover Trial with Integral n-of-1 Design," Pain, 1994, pp. 127-133, 59.
Nelson et al., "High-dose Oral Dextromethorphan Versus Placebo in Painful Diabetic Neuropathy and Postherpetic Neuralgia," Neurology, 1997, pp. 1212-1218, 48(5).
O'Hearn et al., "Administration of a Non-nmda Antagonist, GYKI 52466, Increases Excitotixic Purkinje Cell Degeneration Caused by Ibogaine," Neuroscience, 2004, pp. 373-383, 127(2).
O'Hearn et al., "Degeneration of Purkinje Cells in Parasagittal Zones of the Cerebellar Vermis After Treatment with Ibogaine or Harmaline," Neuroscience, 1993, pp. 303-310, 55.
O'Hearn et al., "Ibogaine Induces Glial Activation in Parasagittal Zones of the Cerebellum," Neuroreport, 1993, pp. 299-302, 4.
O'Hearn et al., "The Olivocerebellar Projection Mediates Ibogaine-induced Degeneration of Purkinje Cells: A Model of Indirect, Trans-synaptic Excitotoxicity," J Neurosci, 1997, pp. 8828-8841, 17.
Paralyzed Veterans of America, "PVA in Action," PN/Paraplegia News, Research & Education—Research Projects Approved, Aug. 1997, pp. 52-57.
Paralyzed Veterans of America, "PVA in Action," PN/Paraplegia News, Research & Education—SCRF Projects Approved for Funding, Feb. 1996, pp. 57-60.
Paralyzed Veterans of America, Spincal Cord Research Foundation, "Guidelines and Procedures for Research Projects Designed to Develop Treatments for Paralysis and Improve the Lives of Individuals with Paralysis Until Therapies Become Available," 1996, pp. 7 pages.
Plannells-Cases et al., "Small Molecules Targeting the NMDA Receptor Complex as Drugs for Neuropathic Pain," Mini Reviews in Medicinal Chemistry, 2003, pp. 749-756, 3.
Rogawski, "Therapeutic Potential of Excitatory Amino Acid Antagonists: Channel Blockers and 2,3-Benzodiazepines," Trends Pharmacol Sci, 1993, pp. 325-331, 14.
Sang et al., "AMPA/Kainate Antagonist LY293558 Reduces Capsaicin-evoked Hyperalgesia but Not Pain in Normal Skin in Humans," Anesthesiology, Nov. 1998, pp. 1060-1067, 89(5).
Sang et al., "Dextromethorphan and Memantine in Painful Diabetic Neuropathy and Postherpetic Neuralgia: Efficacy and Dose-response Trials," Anesthesiology, 2002, pp. 1053-1061, 96(5).
Sang et al., American Pain Society Poster Abstract, No. 661, "A Double-Blinded Randomized Controlled Trial of Dextromethorphan Versus Memantine Versus Active Placebo in Patients with Painful Diabetic Neuropathy and Post-herpetic Neuralgia," 1997, pp. 111.
Sang, "NMDA-Receptor Antagonists in Neuropathic Pain: Experimental Methods to Clinical Trials," Journal of Pain and Symptom Management, Jan. 2000, pp. S21-S25, 19(1).
Coghill & Sang et al, "Pain Intensity Processing Within the Human Brain: A Bilateral, Distributed Mechanism," J Neurophysiol, 1999, pp. 1934-1943, 82.
Sang, American Pain Society, "New Drug Treatments for Neuropathic Pain: A Critical Look at Recent Clinical Trials of Blockers of Excitatory Amino Acid Receptors or Sodium Channels (Symposium)," Poster, 1997.
Coghill & Sang, American Pain Society, "PET Analysis of Supraspinal Processing of Ischemic Pain and Post-Ischemic Dysethsias (Poster)," Poster, 1997.
Shin et al., "Neuropsychotoxicity of Abused Drugs: Potential of Dextromethorphan and Novel Neuroprotective Analogs of Dextromethorphan with Improved Safety Profiles in Terms of Abuse and Neuroprotective Effects," Journal of Pharmacological Sciences, 2008, pp. 22-27, 106.

Sindrup et al., "Efficacy of Pharmacological Treatments of Neuropathic Pain: An Update and Effect Related to Mechanism of Drug Action," Pain, 1999, pp. 389-400, 83(3).

Suzuki et al., "Comparison of the Effects of MK-801, Ketamine and Memantine on Responses of Spinal Dorsal Horn Neurones in a Rat Model of Mononeuropathy," Pain, Mar. 2001, pp. 101-109, 91(1/2), ISSN: 0304-3959.

U.S. National Library of Medicine and the National Institute of Health, Medline Plus Drug Information: Dextromethorphan, pp. 1-7, last retrieved Aug. 13, 2008.

Welsh et al., "Why Do Purkinje Cells Die So Easily After Global Brain Ischemia? Aldolase C, EAAT4, and the Cerebellar Contribution to Posthypoxic Myoclonus," Adv Neurology, 2002, pp. 331-359, 89.

Wiley et al, "Affinity and Specificity of N-Methyl-D-Aspartate Channel Blockers Affect Their Ability to Disrupt Prepulse Inhibition of Acoustic Startle in Rats," Psychopharmacology, 2003, pp. 378-385, 165.

Wrathall et al., "Effect of Kynurenate on Functional Deficits Resulting from Traumatic Spinal Cord Injury," European Journal of Pharmacology, 1992, pp. 273-81, 218(2-3).

Wyeth Consumer Healthcare, Robitussin Product Labeling—Robitussin CoughGels Long-Acting, pp. 1-2, last retrieved Aug. 13, 2008.

Wyeth Consumer Healthcare, Robitussin Product Labeling—Robitussin Pediatric Cough Long-Acting, pp. 1-2, last retrieved Aug. 13, 2008.

Wyeth Consumer Healthcare, Robitussin Product Labeling—Robitussin Cough DM, pp. 1-2, last retrieved Aug. 13, 2008.

Wyeth Consumer Healthcare, Robitussin Product Labeling—Robitussin Cough Long-Acting, pp. 1-2, last retrieved Aug. 13, 2008.

Wyeth Consumer Healthcare, Robitussin Product Labeling—Robitussin Cough Sugar-Free DM, pp. 1-2, last retrieved Aug. 13, 2008.

"Package insert for Neurotin® (gabapentin)", printed from www.accessdata.fda.gov, dated Apr. 2009.

Attal, N., "Pharmacologic treatment of neuropathic pain," 2001, *Acta neurol. belg.* 101:53-64.

Bern, J. and Peck, R., "Dextromethorphan. An overview of safety issues," 1992, *Drug Safety* 7(3):190-199.

Carliss, R.D. et al., "Oral administration of dextromethorphan does not produce neuronal vacuolation in the rat brain," 2007, *NeuroToxicology* 28:813-818.

Childers, W. and Baudy, R., "$N$-Methyl-$_D$-Aspartate antagonists and Neuropathic Pain: The Search for Relief," 2007, *J. Med. Chem.* 50:2557-2562.

Lipton, S., "Failures and Successes of NMDA Receptor Antagonists: Molecular Basis for the Use of Open-Channel Blockers like Memantine in the Treatment of Acute and Chronic Neurologic Insults," 2004, *J of the American Society for Experimental Neuro Therapeutics* 1:101-110.

Lograsso, P. and Mckelvy, J., "Advances in pain therapeutics," 2003, *Current Opinion in Chemical Biology* 7:452-456.

Nelson, K.A. et al., "High-dose oral dextromethorphan versus placebo in painful diabetic neuropathy and postherpetic neuralgia," 1997, *Neurology* 48(5):1212-8.

Sindrup, S. and Jenson, T., "Efficacy of pharmacological treatments of neuropathic pain: an update and effect related to mechanism of drug action," 1999, *Pain* 83:389-400.

Weinbroum, A. et al., "The role of dextromethorphan in pain control," 2000 *Can. J. Anesth.* 47(6):585-596.

Altier and Stewart, "The Role of Dopamine in the Nucleus Accumbens in Analgesia" (1999) *Life Sciences* 65(22):2269-2287.

Burkey et al., "Dopamine Reuptake Inhibition in the Rostral Agranular Insular Cortex Produces Antinociception" (1999) *J. of Neuroscience* 19(10):4169-4179.

Consumer Healthcare Products Association, "Briefing Book for the Meeting of the FDA Drug Safety and Risk Management Committee" (2010).

Gelgor et al., "Injectable Aspirin and Mepyramine Abolish Post-Ischaemic Hyperalgesia in Rats" (1986) *Pain* 26:353-359.

Klein, M., "Overview of the Sep. 14, 2010, DSaRM Advisory Committee Meeting to Discuss the Drug Enforcement Administration (DEA) Request for an Abuse Potential Evaluation and Scheduling Recommendation for Dextromethorphan (DXM)" (2010) *Memorandum from Dept. of Health and Human Services FDA Center for Drug Evaluation and Research Office of the Center Director*.

Muir, K., "Glutamate-based therapeutic approaches: clinical trials with NMDA antagonists" (2006) *Curr. Opin. In Pharmacology* 6:53-60.

Raffa, R., "Antihistamines as analgesics" (2001) *J. of Clinical Pharmacy and Therapeutics* 26:81-85.

Rumore et al., "Clinical Efficacy of Antihistaminics as Analgesics" (1986) *Pain* 25:7-22.

Xia et al., "Comparison of Effects of Lidocaine Hydrochloride, Buffered Lidocaine, Diphenhydramine, and Normal Saline After Intradermal Injection" (2002) *J. of Clinical Anesthesia* 14:339-343.

"Guidance for Industry Estimating the Maximum Safe Starting Dose in Initial Clinical Trials for Therapeutics in Adult Healthy Volunteers" *Office of Training and Communications, Division of Drug Information*, FDA, Rockville, MD, US Dept. of Health and Human Services, Jul. 2005.

Letter from Rick Finklestein, dated Sep. 7, 2011; (referred to in Office Action Response dated Nov. 4, 2011).

Letter from Florence C. Barnett, MD, FACS, dated Sep. 8, 2011; (referred to in Office Action Response dated Nov. 4, 2011).

Letter from Laura George, dated Oct. 31, 2011; (referred to in Office Action Response dated Nov. 4, 2011).

Advokat et al., "Potentiation of morphine-induced antinociception in acute spinal rats by the NMDA antagonist dextrorphan," Brain Research, vol. 699, No. 1, 1995, pp. 157-160.

Eide, P. K., "Pathophysiological mechanisms of central neuropathic pain after spinal cord injury," Spinal Cord 1998 GB, vol. 36, No. 9, 1998, pp. 601-612.

Extended European Search Report, EP 10183424.0, mailed on Oct. 26, 2011.

Laughlin et al., "Spinally administered dynorphin A produces long-lasting allodynia: Involvement of NMDA but not opioid receptors," Pain 1997, vol. 72, No. 1-2, pp. 253-260.

Mercadante, S., "Gabapentin in spinal cord injury pain," Pain Clinic 1998 NL, vol. 10, No. 3, 1998, pp. 203-206.

Siddall et al., "Pain associated with spinal cord injury," Current Opinion in Neurology 1995, vol. 8, No. 6, 1995, pp. 447-450.

Hao et al., "Treatment of a Chronic Allodynia-Like Response in Spinally Injured Rats: Effects of Systemically Administered Excitatory Amino Acid Receptor Antagonists," Pain, Elsevier Science Publishers 1996, vol. 66, No. 2/03, pp. 279-285.

Chaplan et al., "Efficacy of spinal NMDA receptor antagonism in formalin hyperalgesia and nerve injury evoked allodynia in the rat," Journal of Pharmacology 1997, vol. 280, No. 2, pp. 829-838.

\* cited by examiner

| | |
|---|---|
| Time Since Injury (years; median, range) | 7.6 (0.3-54) |
| Duration of Pain (years; median, range) | 6.0 (0.6-54) |
| Distribution of allodynia: Segmental (%) | 64 |
| Below level (%) | 36 |
| Extent of spinal cord injury: | |
| Complete (%) | 44 |
| Incomplete (%) | 56 |
| Level of SCI: Cervical (%) | 47 |
| Thoracic (%) | 42 |
| Lumbar (%) | 12 |
| Baseline Average Daily Pain Score (Gracely Scale) | 13 |
| Pain Quality | |
| Burning (%) | 84 |
| Aching (%) | 72 |
| Paresthesias (%) | 88 |
| Shooting/Stabbing (%) | 70 |
| Cold Pain (%) | 28 |
| Constricting (%) | 47 |
| Mechanical Allodynia (%) | 84 |
| Cold Allodynia (%) | 72 |
| Heat Hyperalgesia (%) | 37 |

FIG. 1

|  | Treatment Sequence Group | | | | | | | | Combined | |
| --- | --- | --- | --- | --- | --- | --- | --- | --- | --- | --- |
|  | 1 | | 2 | | 3 | | 4 | | | |
|  | n | % | n | % | n | % | n | % | n | % |
| Total Subjects | 4 |  | 6 |  | 4 |  | 4 |  | 18 |  |
| Sex | | | | | | | | | | |
| Male | 3 | 75.0 | 4 | 66.7 | 4 | 100.0 | 4 | 100.0 | 15 | 83.3 |
| Female | 1 | 25.0 | 2 | 33.3 | 0 | 0.0 | 0 | 0.0 | 3 | 16.7 |
| Race | | | | | | | | | | |
| White | 4 | 100.0 | 6 | 100.0 | 4 | 100.0 | 4 | 100.0 | 18 | 100.0 |
| Age (Years) | | | | | | | | | | |
| Mean | | 47.25 | | 57.17 | | 50.00 | | 49.50 | | 51.67 |
| Std Error | | 7.18 | | 2.60 | | 5.16 | | 6.59 | | 2.53 |
| Baseline Gracely Scale | | | | | | | | | | |
| Mean | | 13.22 | | 13.81 | | 15.99 | | 13.24 | | 13.97 |
| Std Error | | 1.03 | | 1.23 | | 1.07 | | 1.11 | | 2.72 |
| Presence of Allodynia | 3 | 75.0 | 5 | 83.3 | 2 | 50.0 | 4 | 100.0 | 14 | 77.8 |
| Concomitant Analgesic | | | | | | | | | | |
| Amitriptyline | 0 | 0.0 | 2 | 33.3 | 0 | 0.0 | 1 | 25.0 | 3 | 16.7 |
| Paroxetine | 0 | 0.0 | 0 | 0.0 | 0 | 0.0 | 1 | 25.0 | 1 | 5.6 |
| Clonazepam | 0 | 0.0 | 1 | 16.7 | 1 | 25.0 | 0 | 0.0 | 2 | 11.1 |
| Carbamazepine | 1 | 25.0 | 1 | 16.7 | 1 | 25.0 | 0 | 0.0 | 3 | 16.7 |
| Aspirin | 1 | 25.0 | 2 | 33.3 | 0 | 0.0 | 0 | 0.0 | 3 | 16.7 |
| Ibuprofen | 2 | 50.0 | 1 | 16.7 | 1 | 25.0 | 1 | 25.0 | 5 | 27.8 |
| Naproxen | 0 | 0.0 | 1 | 16.7 | 0 | 0.0 | 0 | 0.0 | 1 | 5.6 |
| Hydrocodone-APAP | 0 | 0.0 | 1 | 16.7 | 0 | 0.0 | 0 | 0.0 | 1 | 5.6 |

"Treatment Sequence" refers to the order of treatments, where each treatment follows every other treatment only once:

1 = Dextromethorphan—gabapentin—combination—placebo
2 = Gabapentin—Dextromethorphan—placebo—combination
3 = Combination—gabapentin—placebo—dextromethorphan
4 = Placebo—dextromethorphan—combination—gabapentin

FIG. 2

|  | Treatment | | | | P Value | | | | | | |
|---|---|---|---|---|---|---|---|---|---|---|---|
|  | Combination | Dex | Gaba | Placebo | Combination vs. | | | Dex vs. | | Gaba vs. | |
|  |  |  |  |  | Dex | Gab a | Plac | Gab | Plac | Plac | |
| Global Pain Intensity | | | | | | | | | | | |
| Spontaneous Pain[1] | 8.78 ± 1.25 | 9.28 ± 1.16 | 9.06 ± 1.02 | 12.72 ± 0.91 | 0.78 | 0.96 | 0.002 | 0.82 | 0.003 | 0.002 | |
| Touch-Evoked Allodynia[1] (n=14) | 4.57 ± 1.23 | 6.21 ± 1.50 | 6.14 ± 1.38 | 9.07 ± 1.61 | 0.20 | 0.38 | 0.001 | 0.68 | 0.03 | 0.01 | |
| Global Pain Relief | | | | | | | | | | | |
| Relief[2] | 3.83 ± 0.31 | 3.50 ± 0.28 | 3.22 ± 0.31 | 2.17 ± 0.25 | 0.27 | 0.04 | <0.001 | 0.30 | <0.001 | <0.001 | |
| Patient Satisfaction[3] | 2.56 ± 0.29 | 2.44 ± 0.28 | 2.06 ± 0.24 | 1.28 ± 0.18 | 0.88 | 0.13 | <0.001 | 0.16 | <0.001 | 0.01 | |

Values are mean ± SD
[1] 20-point Gracely Scale
[2] Complete relief = 6; a lot of relief = 5; moderate relief = 4; slight relief = 3; no relief = 2; pain worse = 1
[3] Excellent = 5; very good = 4; good = 3; fair = 2; poor = 1

FIG. 4

|  | Treatment | | | | P Value | | | | | | |
|---|---|---|---|---|---|---|---|---|---|---|---|
|  | Combination | Dex | Gaba | Placebo | Combination vs. | | | Dex vs. | | Gaba vs. | |
|  |  |  |  |  | Dex | Gaba | Plac | Gaba | Plac | Gaba | Plac |
| Functional Classification | | | | | | | | | | | |
| Incomplete | | | | | | | | | | | |
| Mean | 11.37 ± 1.50 | 13.97 ± 1.12 | 12.57 ± 1.20 | 14.91 ± 0.82 | 0.16 | 0.59 | 0.04 | 0.38 | 0.48 | 0.12 | |
| n | 9 | 9 | 9 | 9 | | | | | | | |
| Complete | | | | | | | | | | | |
| Mean | 11.71 ± 1.38 | 11.86 ± 1.58 | 13.26 ± 0.90 | 12.93 ± 1.19 | 0.51 | 0.008 | 0.03 | 0.03 | 0.13 | 0.47 | |
| n | 9 | 9 | 9 | 9 | | | | | | | |
| Distribution of Pain | | | | | | | | | | | |
| Segmental | | | | | | | | | | | |
| Mean | 11.32 ± 1.34 | 11.48 ± 1.51 | 12.81 ± 0.85 | 12.43 ± 1.11 | 0.52 | 0.01 | 0.04 | 0.05 | 0.13 | 0.61 | |
| n | 9 | 9 | 9 | 9 | | | | | | | |
| Diffuse | | | | | | | | | | | |
| Mean | 9.80 ± 1.78 | 13.14 ± 1.41 | 11.04 ± 1.16 | 14.58 ± 0.90 | 0.40 | 0.80 | 0.13 | 0.27 | 0.50 | 0.08 | |
| n | 6 | 6 | 6 | 6 | | | | | | | |
| Presence of Evoked Pain | | | | | | | | | | | |
| Allodynia | | | | | | | | | | | |
| Mean | 9.72 ± 1.22 | 10.48 ± 1.23 | 11.01 ± 0.90 | 13.36 ± 1.00 | <0.001 | 0.02 | <0.001 | 0.03 | <0.001 | <0.001 | |
| n | 14 | 14 | 14 | 14 | | | | | | | |
| No allodynia | | | | | | | | | | | |
| Mean | 14.15 ± 1.37 | 14.57 ± 1.78 | 15.88 ± 1.22 | 15.83 ± 1.39 | <0.001 | <0.001 | <0.001 | 0.12 | 0.006 | 0.006 | |
| n | 4 | 4 | 4 | 4 | | | | | | | |

Values are mean ± SD

FIG. 5

TREATMENT OF CENTRAL NEUROPATHIC PAIN

RELATED APPLICATION

This application claims the benefit of U.S. Provisional Application Ser. No. 60/297,145, filed Jun. 7, 2001, the entire teachings of which are incorporated herein by reference.

BACKGROUND OF THE INVENTION

Humans with injury to the central nervous system (e.g., brain and spinal cord) can suffer from chronic central neuropathic pain. However, standard analgesics, such as nonsteroidal anti-inflammatory drugs, opioids, tricyclic antidepressants, anticonvulsants and antispasmodics, are ineffective in relieving the chronic central neuropathic pain, in particular pain associated with spinal cord injury. Further, relief of pain by certain analgesics can result in adverse side effects such as fatigue, confusion, dizziness, somnolence and speech difficulty thereby diminishing the attractiveness of the analgesic to the human. Thus, there is a need to develop new, improved and effective methods of treatments for pain in humans with central nervous system injury which alleviate pain without adverse side effects.

SUMMARY OF THE INVENTION

The present invention relates to a method of treating chronic central neuropathic pain in humans suffering from spinal cord injury by administering an N-methyl-D-aspartate (NMDA) receptor antagonist.

In one embodiment, the method is treatment of central neuropathic pain in a human, the method including administering to the human an analgesic composition, wherein the improvement comprises chronic administration to the human an analgesic composition that consists essentially of an N-methyl-D-aspartate receptor antagonist and wherein there is essentially no high affinity N-methyl-D-aspartate receptor antagonist in the analgesic composition.

In another embodiment, the method is for treating central neuropathic pain in a human, the method including administering to the human an analgesic composition, wherein the improvement comprises administering to the human an analgesic composition that consists essentially of an N-methyl-D-aspartate receptor antagonist, and wherein the N-methyl-D-aspartate receptor antagonist essentially does not include ketamine or a subtype selective N-methyl-D-aspartate receptor antagonist.

In an additional embodiment, the invention is the use of an N-methyl-D-aspartate receptor antagonist, or component thereof for the manufacture of a medicament that includes an analgesic component that consists essentially of the N-methyl-D-aspartate receptor antagonist, for the chronic treatment of central neuropathic pain.

In still another embodiment, the method is treating central neuropathic pain in a human, comprising the step of acutely administering to the human an analgesic composition that consists essentially of an N-methyl-D-aspartate receptor antagonist, and wherein the N-methyl-D-aspartate receptor antagonist essentially does not include ketamine.

In yet another embodiment, the method is treating central neuropathic pain in a human, comprising chronically administering to the human an analgesic composition that consists essentially of an N-methyl-D-aspartate receptor antagonist and wherein there is essentially no high affinity N-methyl-D-aspartate receptor antagonist in the analgesic composition.

In a further embodiment, the method is treating central neuropathic pain in a human, comprising the step of administering to the human an analgesic composition that consists essentially of an N-methyl-D-aspartate receptor antagonist, and wherein the N-methyl-D-aspartate receptor antagonist essentially does not include ketamine or a subtype selective N-methyl-D-aspartate receptor antagonist.

The invention described herein provides a method of treating chronic neuropathic pain in a human suffering from a spinal cord injury by administering NMDA receptor antagonists. Advantages of the method of the invention include, for example, augmented pain relief with no or significantly reduced side effects (e.g., fatigue, confusion, dizziness, somnolence and speech difficulty) particularly in humans where pain management strategies are difficult to implement. The methods of the invention provide an efficient way to treat and reduce the severity of central neuropathic pain in a human suffering from a spinal cord injury.

Thus, treatment of humans with a spinal cord injury who have central neuropathic pain with NMDA receptor antagonists can diminish their pain without intolerable side effects.

BRIEF DESCRIPTION OF FIGURES

FIG. 1 lists the clinical characteristics of human patients (n=28) with central neuropathic pain.

FIG. 2 lists the demographic characteristics of human patients (n=18) in the four treatment groups.

FIG. 4 is a summary of Global Pain Intensity and Pain Relief Measures in human patients (n=18) in the four treatment groups rated on the last day of each treatment.

FIG. 5 lists the mean pain intensities over each five week treatment period in each of the four treatment groups based on functional classification, distribution of pain and presence of evoked pain.

DETAILED DESCRIPTION OF THE INVENTION

Figure 3:
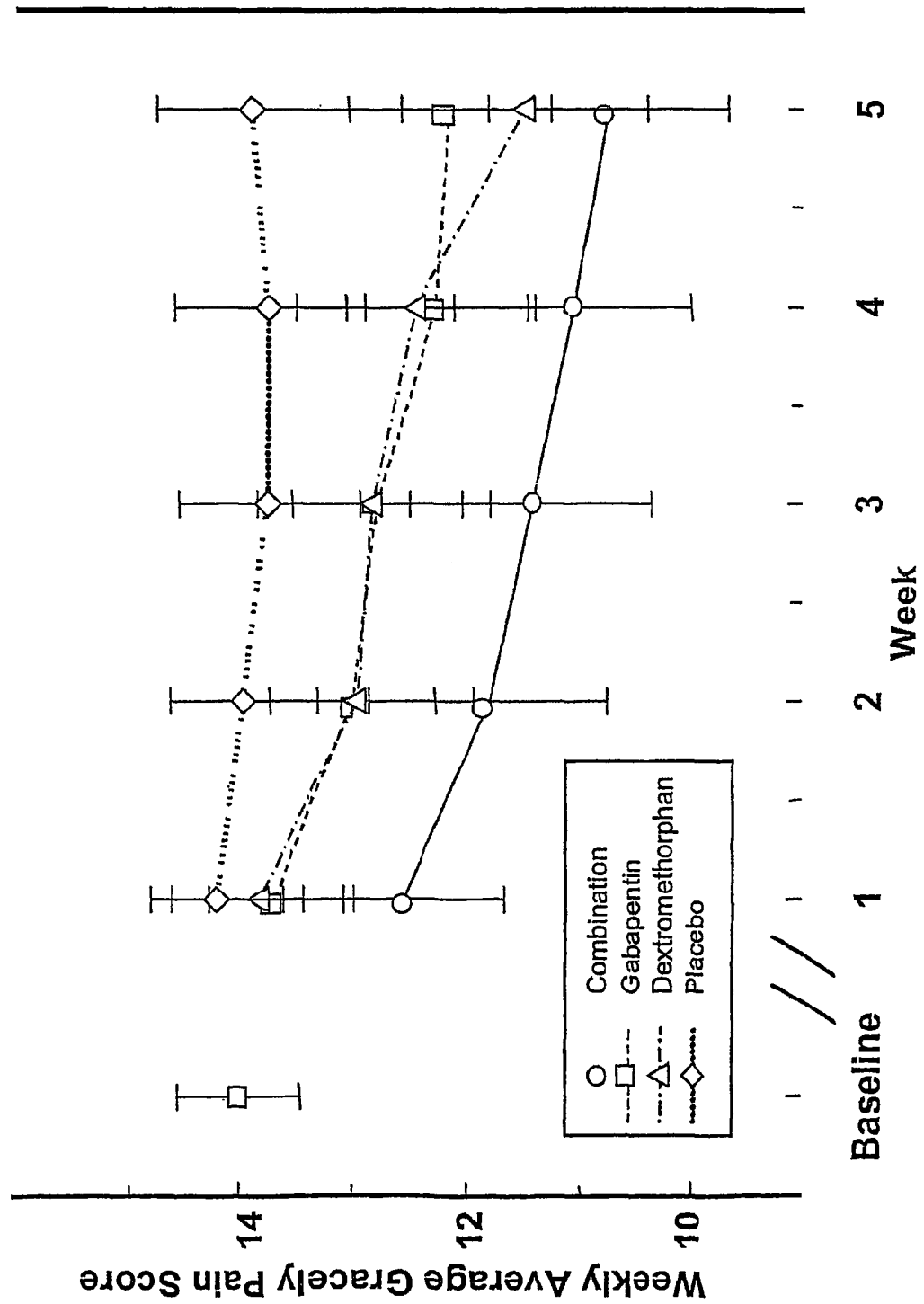
FIG. 3 depicts the weekly average Gracely pain score for human patients in the four treatment groups.
Figure 6:
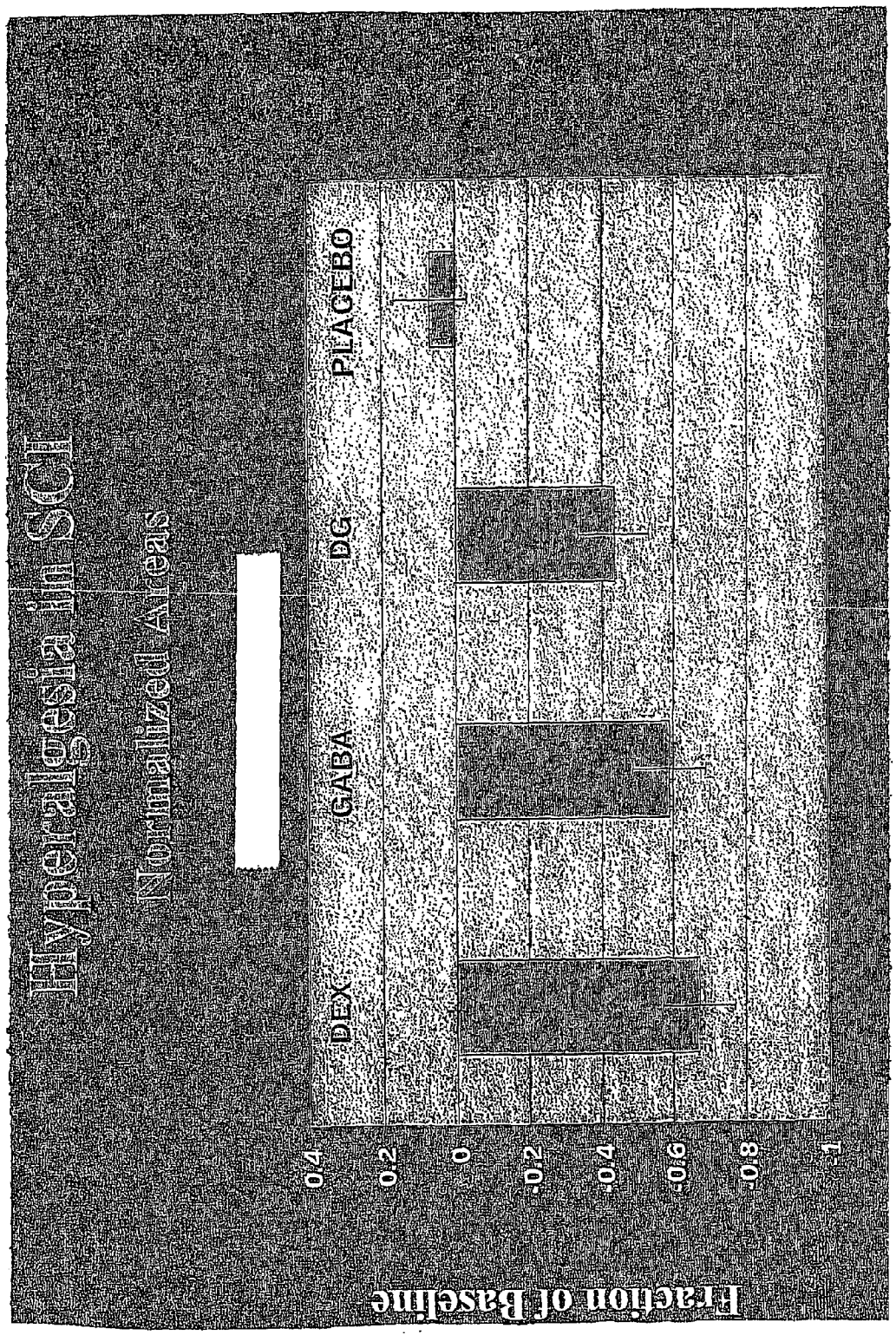
FIG. 6 depicts hyperalgesia in human patients treated with dextromethorphan alone (DEX), gabapentin alone (GABA) or a dextromethorphan/gabapentin combination (DG) compared to the placebo treatment group.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to the discovery that treatment with NMDA receptor antagonists decrease central neuropathic pain of humans. In particular, the chronic administration of an NMDA receptor antagonist (e.g., dextromethorphan hydrobromide) has been found to decrease chronic central neuropathic pain in humans following spinal cord injury with no or significantly diminished side effects.

The NMDA receptor antagonists can be high affinity NMDA receptor antagonists (e.g., ketamine), low affinity NMDA receptor antagonists, such as dextromethorphan hydrobromide (also referred to herein as "dextromethorphan"), amantadine, memantine, remacemide, riluzole; and opioids with NMDA activity (e.g., Ketobemidone, methadone, dextropropoxyphene, meperidine).

"Central neuropathic" pain refers to pain associated with a disorder, congenital defect or injury of the central nervous system (the brain or spinal cord). The central neuropathic pain can be spontaneous or invoked pain. "Central neuropathic" pain can be chronic or acute. Chronic neuropathic pain typically is pain of a duration greater than three months.

The central neuropathic pain can be in a human suffering from a stroke, a brain lesion or a spinal cord injury. For example, the spinal cord injury can be the result of trauma to the spinal cord either as a result of direct anatomical disruption of spinal cord or associated spinal cord damage in Syringomyelia. Additionally, or alternatively, the central neuropathic pain can be the result of a lesion, Multiple sclerosis, a tumor within or surrounding the spinal cord or a vascular lesion compressing the spinal cord.

"Spinal cord injury" refers to any trauma, damage or wound to any level (e.g., cervical, thoracic, lumbar, sacral) of the spinal cord. The spinal cord injury can also be a congenital defect. Using standard medical criteria, one of skill in the art would be capable of diagnosing a human with a central neuropathic pain spinal cord injury.

An "analgesic amount" or "analgesic dose" is the quantity of NMDA receptor antagonist which relieves the pain perceived by the human undergoing treatment with the NMDA receptor antagonist. In a preferred embodiment, the analgesic amount is an amount of an NMDA receptor antagonist, such as dextromethorpan, in a range between about greater than 120 mg/day and about 1200 mg/day.

"Chronic administration" is wherein a single dose is not effective in alleviating central neuropathic pain. Chronic administration can be, for example, the administration of an NMDA receptor antagonist, such as dextromethorpan hydrobromide, for 21 or more days. The NMDA receptor antagonist can be chronically administered by administration an initial dose then a subsequent dose. "Acute administration" is administration of a dosage that is effective at alleviating central neuropathic pain in a single dose, whether the administration is a single bolus, such as pills or an intramuscular injection, or continuously within a limited period of time, such as by intravenous administration.

In particular the invention relates to a method of treating a human with a spinal cord injury suffering from central neuropathic pain by titrating the dose of NMDA receptor antagonist to an analgesic dose which results in minimal side effects (e.g., fatigue, confusion, dizziness, somnolence and speech difficulty). Titration of the dose of NMDA receptor antagonist is accomplished administering to the human an initial dose of NMDA receptor antagonist (e.g., 120 mg/day) followed by an evaluation by the human undergoing treatment of their pain and side effects. A subsequent dose of NMDA receptor antagonist is administered to the human until the pain perceived by the human is relieved or tolerable. In a preferred embodiment, the dose of NMDA receptor antagonist is increased in increments of about 60 mg/day. The method further includes maintaining the human on a dose of NMDA receptor antagonist which results in analgesia with minimal side effects.

NMDA receptor antagonists are compounds capable of competing with or counteracting the effect of NMDA receptors. In a preferred embodiment, the NMDR receptor antagonist is dextromethorphan. Dextromethorphan is widely available.

Central neuropathic pain can also be treated with subtype specific NMDA receptor antagonists. In a preferred embodiment, administration of the subtype specific NMDA receptor antagonist is used to treat a spinal cord injury, for example, as a result of a trauma to the spinal cord either (e.g., as a result of direct anatomical disruption of spinal cord or associated spinal cord damage in Syringomyelia) a tumor within or surrounding the spinal cord or a vascular lesion compressing the spinal cord.

The methods of the invention can be accomplished by the administration of the NMDA receptor antagonist by enteral or parental means. A preferred method of administration is by oral ingestion of a capsule, tablet or drink. Alternatively, or additionally, the NMDA receptor antagonist can be administered intramuscularly or intraperitoneally. The NMDA receptor antagonists can be administered alone or as admixtures with conventional excipients (e.g., water, salt solutions) which do not deleteriously react with the NMDA receptor antagonist.

The present invention is further illustrated by the following examples, which are not intended to be limiting in any way.

EXEMPLIFICATION

Approximately 183,000 to 230,000 persons in the United States have sustained spinal cord injuries (SCI) (DeVivo M J, et al. Arch Neurol. 37:707-708 (1980); Harvey C, et al. Paraplegia 28:537-544 (1990); Lasfarques J E, et al. Paraplegia 33:62-68 (1995)). Direct injury to the spinal cord can result in a chronic neuropathic pain condition, typically described as constant "burning," "tight," "constricting," and/or "shooting and stabbing," often in combination with pain due to a stimulus which does not normally evoke pain (allodynia), or augmented pain to a normally pail stimulus (hyperalgesia). Central neuropathic pain following SCI generally occurs in one of two anatomic distributions: 1) Circumferential ("band-like"), at the border of normal sensation and anesthetic skin; and 2) below the level of the spinal cord lesion, perceived diffusely in anesthetic regions (Siddall P J, et al. Spinal Cord 35(2):69-75 (1997)). The prevalence of chronic pain following SCI has been reported to vary between 34%[5] and 90% (Botterell E H, et al. Proc R Soc Med. 47:281-288 (1953)). Importantly, disability associated with SCI more often is due to its associated pain rather than loss of function (Rose M, et al. Pain 34:101-102(1988)). and may be a major factor in causing unemployment and depression. (Ravenscroft A, et al. Spinal Cord 38(10):611-4 (2000)).

There is currently no chronically-administered analgesic regimen that has systematically been shown to be effective for the treatment of chronic central neuropathic pain following SCI. Results of the few randomized controlled trials evaluating chronic oral agents in SCI pain have been negative, including studies of valproate (Drewes A M, et al. Paraplegia 32:565-569(1994)), mexiletine (Chiou-Tan F Y, et al. Am J Phys Med Rehabil. 75:84-87 (1996)), and trazodone (Davidoff G, et al., Pain 29:151-161 (1997)).

Data in animal models of SCI have shown that restricting the extent of excitotoxicity after SCI with NMDA receptor antagonists could alleviate behaviors associated with spontaneous pain and hyperalgesia, the behavioral correlate of central nervous system excitation (Liu S, et al. Brain Res. 756: 160-167 (1997); Bennett A D, et al. Brain Res. 859:72-82 (2000); Hao J X, et al. Pain 45:175-185 (1991); and Hao J X, and Xu X J. Pain 66:279-285 (1996)). Specifically, a study by Hao and Xu (Hao J X, and Xu X J. Pain 66:279-285 (1996)) have shown that, of a series of NMDA receptor antagonists, only dextromethorphan preserves motor function in spinally injured rats at doses that relieved touch-evoked pain. However, the clinical data in patients with peripheral neuropathic pain show a marginal effect (Nelson K A, et al. Neurology 48:1212-1218 (1997) and Sang C N, et al. American Pain Society Abstracts, 1997)).

In patients (also referred to herein as "human" or "human patient"), a recent study evaluating the acute parenteral administration of the NMDA receptor antagonist ketamine (Eide P K, et al. Neurosurg. 37:1080-1087(1995)) reduced both spontaneous and evoked SCI pain, but ketamine has limited clinical utility because of its psychotomimetic side effects. Repeated doses of the antiepileptic agent gabapentin, whose mechanism is still being elucidated, also alleviated chronic hypersensitivity in spinally injured rats (Hao, J X, et al. Neurosci Lett 280(3):211-4 (2000)). To date, there are no data which systematically demonstrate an effect of either dextromethorphan or gabapentin on central neuropathic pain.

Moreover, the simultaneous use of multiple standard analgesics is the most frequent form of treatment in central and peripheral neuropathic pain states, and there has until now been no systematic approach to assess combination therapy. The present study is based on the hypothesis that the use of combinations of drugs acting through different pharmacologic mechanisms may result in an augmented analgesia without augmented toxicity. A single-center, randomized, double-blind, double-dummy, 2×2 factorial crossover study evaluating the combination of dextromethorphan and gabapentin, dextromethorphan alone, gabapentin alone, and placebo in the treatment of central neuropathic pain following traumatic spinal cord injury was performed.

Central neuropathic pain following traumatic spinal cord injury (SCI) may be severe and refractory to standard analgesics. Pharmacologic agents that target distinct pathophysiological pain mechanisms theoretically could provide pain relief for these patients. The analgesic efficacy of dextromethorphan and gabapentin in combination, dextromethorphan alone, gabapentin alone, and placebo, in patients with pain following SCI was evaluated in a randomized, double-blind, double-dummy, 2×2 factorial, Latin Square crossover trial, we evaluated the four treatments. Each treatment was titrated over 4 weeks and maintained at the individual's minimum intolerated dose until the end of Week 5. Each treatment period was followed by a 1-week washout period or until pain returned to baseline. Primary efficacy measure was mean pain intensity during the 5-week treatment period, measured by the 20-point Gracely pain intensity scale.

Eighteen of 23 randomized subjects completed all 4 treatments. Mean daily doses were 416 mg for dextromethorphan, 2657 mg for gabapentin, and 401 mg of dextromethorphan with 2007 mg of gabapentin for the combination. The combination resulted in significantly reduced pain intensities over dextromethorphan ($p=0.004$), gabapentin ($p=0.02$), and placebo ($=0.001$) during Week 1, which persisted to Week 4. During Week 5, the combination significantly reduced mean pain intensities of gabapentin only ($=0.02$). Eleven of 18 (61%) patients receiving the combination had at least moderate or better pain relief, in contrast to that of dextromethorphan 9/18 (50%), gabapentin 7/18 (39%), and placebo 2/18 (11%). Pain relief scores for the combination were significantly better than gabapentin ($p=0.04$) but not for dextromethorphan ($p=0.27$). Overall patient satisfaction at the end of each treatment period, which takes into account both side effects and pain relief, was significantly better for dextromethorphan alone ($p<0.001$), gabapentin alone ($p<0.01$) and the combination ($p<0.001$) compared to placebo.

Chronic oral administration of dextromethorphan, gabapentin, and the dextromethorphan-gabapentin combination provided a significant reduction of SCI pain compared to placebo and greater reduction than either component alone. This is the first systematic demonstration of any successful chronic treatment of refractory central pain following SCI.

Methods

Patients

Patients with 1) central neuropathic pain secondary to traumatic SCI in persons >18 years of age, 2) moderate pain for at least 50% of the day for at least 3 months, 3) concurrent use of no more than two analgesics at a stable dose (e.g. tricyclic antidepressants, anticonvulsants, nonsteroidal antiinflammatory drugs, or limited use of low-potency short-acting opioids), and 4) 100% compliance in rating their overall pain intensity 5-times daily in a diary for 1 week, were recruited nationwide between July 1997 and April 1999 using written announcements and by physician referrals.

Exclusion criteria included: 1) Presence of another type of pain of equal severity as that caused by SCI, such as musculoskeletal pain; 2) pregnancy or breast feeding; 3) hepatic or renal dysfunction; 4) significant cardiac disease; 5) signs or symptoms of another central neurological disorder; 6) severe psychological disorder requiring treatment; 7) concurrent use of monoamine oxidase inhibitors or phenothiazines; history of hypersensitivity or intolerance to dextromethorphan or gabapentin; and chronic substance abuse, including alcohol. Women of childbearing potential agreed to use adequate contraception during the study.

The study was in compliance with the Declaration of Helsinki and was approved by the Partners Human Research Committee. All patients gave written informed consent.

Study Design

All patients were followed as outpatients. Patients were randomly assigned to a sequence of the 4 treatments. Each of the 4 treatment periods consisted of 5 weeks. Each treatment period was separated by a 1-week washout period, with the requirement that pain return to baseline level. Dextromethorphan (Endo Inc., Neptune, N.J.; and its externally identical placebo) and gabapentin (Neurontin, Pfizer, Inc., Ann Arbor, Mich.; and its externally identical placebo) were dispensed using a double-dummy design; thus, the dextromethorphan: gabapentin dose-ratio was maintained at 1:5. Subjects started at 120 mg/day of dextromethorphan vs. placebo and 600 mg/day of gabapentin vs. placebo, and titrated according to a fixed schedule until they reached the ceiling doses equivalent to 600 mg/day of dextromethorphan or 3000 mg/day of gabapentin or their maximally tolerated dose (the dose just causing side effects, MTD). The titration regimen and the number of capsules per dose for each treatment were the same in each treatment group, in order to maintain double blinded conditions.

A nurse-clinician blinded to the study drug called each patient at least twice-weekly to instruct each patient on dose increases, encourage compliance, encourage consistency in dosage of concurrent analgesics, assess side effects, and answer any questions relating to the study protocol. Up to 2,000 mg of acetaminophen were allowed as rescue medication, on a case-by-case basis, for pain intensity scores of 18/20 or higher.

Endpoints

The primary endpoint was mean spontaneous pain intensity averaged weekly, from the start of study drug until the end of Week 5 for each treatment period and overall for the 5 weeks, assessed in a diary in which pain ratings were recorded 5-times daily, and evaluated with the 20-point Gracely pain scale based on 13 words ("faint" to "extremely intense") (Gracely R H, et al. Pain 5:5-18(1978)).

Secondary endpoints were assessed at a clinic visit on the final day of each treatment period, and included: 1) Global Pain Intensity (6-item categorical scale); 2) Global Pain Relief (6-item categorical scale); 3) pain intensity (Gracely Scale) of individual pain descriptors (burning pain; aching pain; tingling pain; cold pain; brief lancinating pain; deep stabbing pain; constricting pain; and touch-evoked pain (allodynia)); 4) areas of evoked pain: a) allodynia and b) pinprick-evoked hyperalgesia; 5) quality of life, assessed using the Duke Health Profile (Parkerson, G R, et al. Medical Care 28:1056-1069(1990)). 6) Patient Satisfaction (5-item categorical scale); 7) patients' assessment of best treatment. Allodynia was mapped by stroking the skin with the distal 5 mm of the corner of a 2×2 gauze sponge at standard pressure, at a rate of 1 cm/sec. Pinprick-evoked hyperalgesia was mapped using a standard safety pin that was pressed against the skin until dimpling was visible. Ambient temperature was maintained at 24 degrees centigrade. All mapping took place within a 30-minute period. The delineated areas of evoked pain were recorded using photographs of 4 views (anterior/posterior/right lateral/left lateral), which were scanned, and the areas of each of the 4 views were summed to determine the composite area.

Presence and intensity (5-item categorical scale) of adverse effects were assessed continuously using an open question.

Evaluation of Adequacy of Blinding

Patient questionnaires to evaluate the adequacy of blinding of treatments, and whether their answers were influenced by side effects or analgesia, were administered at the completion of each treatment period and at the end of the study.

Statistical Analysis

A difference between mean treatment of "mild" and "moderate" pain, with greater than 80% power was detected. Our sample size of 18 was determined by selecting a Type I error=0.05, Type II error=0.2, and a within-subject standard deviation (SD) of 0.15.

For the weekly average Gracely pain scores, a mixed model repeated measures analysis of variance (ANOVA) was used. In order to conduct pairwise comparisons between treatments at each week, a separate 4×4 Latin Square was built into the overall repeated measures model at each week. To obtain a mean difference between treatments across weeks, the weekly pairwise differences were averaged across weeks using contrasts in the overall repeated measures model. All end of period assessments were analyzed using Latin Square ANOVA. For binomial parameters, differences between treatments were examined using the McNemar Q test. Potential carry over effects were examined using the method of Cochran and Cox (Cochran, W G and G M Cox. *Experimental Designs*. New York: John Wiley & Sons, 1968, pg 135-139)).

Results

Subjects

Twenty-eight subjects were screened; five were not randomized because of an unwillingness to risk potential side effects (1), a predominance of musculoskeletal or overuse pain syndromes (1), and abnormal laboratory tests (3). Twenty-three subjects were each randomized to one of the 4 treatment sequence groups. Their clinical characteristics are listed in FIG. 1. Eighteen of the randomized subjects completed evaluations of all of the four treatments FIG. 2. Median age was 51 (range, 34-68) years; median time since injury was 6.8 (1.7-30.3) years. There were no significant differences between any of the treatment sequence groups or between the intent-to-treat and completer data sets with respect to baseline demographic and clinical characteristics. Of the 5 dropouts (all for unacceptable cognitive side effects), three received 1 treatment (2 received dextromethorphan; 1 received placebo), and two received 2 treatments (combination, dextromethorphan; placebo, combination).

Treatment

After the 4 weeks of titration to MTD, mean doses during Week 5 were 416±34 mg/day (maximum daily dose administered, 470±29 mg/day) for dextromethorphan, 2657±155 mg/day for gabapentin (maximum, 2717±148 mg/day), and 401±32 mg/day of dextromethorphan (maximum, 440±30 mg/day) with 2007±158 mg/day of gabapentin (maximum, 2200±150 mg/day) for the combination. The doses of gabapentin were significantly different when used either alone or in combination ($p=0.001$), while those of dextromethorphan were not ($p=0.72$).

Efficacy

Primary Endpoint

The dextromethorphan-gabapentin combination resulted in significantly reduced spontaneous pain intensities over dextromethorphan alone ($p=0.004$), gabapentin alone ($p=0.02$), and placebo ($p=0.001$) during the first week of therapy (Week 1). The mean pain intensities during both Week 5 and over the entire treatment period were significantly lower for the combination compared to gabapentin (Week 5, $p=0.02$; Weeks 1-5, $p=0.001$). Although the combination was also significantly better during the entire treatment period compared to dextromethorphan (Weeks 1-5, $p=0.001$) the reduction in pain intensity was no longer significant during Week 5. (FIGS. 3, 4 and 5).

FIG. 3 shows the mean pain intensities over each 5-week treatment period for subgroups based on functional classification, distribution of pain, and presence of evoked pain. Eight subjects had both complete SCI (i.e. lacking sacral innervation) and segmental pain; all 8 had allodynia. All subjects with segmental pain had allodynia Five of 9 subjects with complete SCI had allodynia Three subjects had a sacral distribution of pain (data not shown).

Eleven of 18 (61%) patients receiving the combination had at least moderate or better pain relief, in contrast to that of dextromethorphan 9/18 (50%), gabapentin 7/18 (39%), and placebo 2/18 (11%). Pain relief scores for the combination were significantly better than gabapentin ($p=0.04$) but not for dextromethorphan ($p=0.27$). Overall patient satisfaction at the end of each treatment period, which takes into account both side effects and pain relief, was significantly better for dextromethorphan alone ($p<0.001$), gabapentin alone ($p<0.01$) and the combination ($p<0.001$) compared to placebo.

Analyses of potential biases of the crossover design showed no carryover or period effects for intensity of spontaneous pain or intensity of evoked allodynia.

Secondary Endpoints

Spontaneous Pain

Global Pain Intensity (of spontaneous pain), Global Pain Relief, and Patient Satisfaction measures were all significantly better in the combination and in the individual components alone compared to placebo (FIG. 4). The combination was statistically superior to both the placebo and gabapentin alone for the Global Pain Relief rating. Among the descriptors of pain, the intensity of burning pain ($p=0.005$) and brief paroxysms of lancinating pain ($p=0.03$) were both significantly improved with the combination compared to placebo, but we were unable to detect an effect of the individual components. Dextromethorphan alone also provided significant relief for these two types of pain compared to placebo (burning pain, $p=0.001$; brief paroxysms of lancinating pain, $p=0.003$)

Evoked Pain

Intensity of Touch-Evoked Allodynia

Among the 14 subjects with allodynia at their screening visit, the combination and each individual component significantly reduced the intensity of allodynia compared to placebo (dextromethorphan, $p=0.03$, gabapentin, $p=0.01$; combination, $p=0.001$) FIG. 4). of allodynia and hyperalgesia Mean areas of allodynia after treatment were reduced from baseline (362±496 cm$^2$) by 50% for the combination (182±373 cm$^2$), 49% for dextromethorphan (183±321 cm$^2$), 71% for gabapentin (106±231 cm$^2$); they were increased by 6% for placebo (383±557 cm$^2$). Mean areas of pinprick hyperalgesia after treatment were reduced from baseline (371±523 cm$^2$) by 43% for the combination (210±421 cm$^2$), 67% for dextromethorphan (122±287 cm$^2$), 59% for gabapentin (152±332 cm$^2$); they were increased by 7% for placebo (395±586 cm$^2$). There was a significant difference in areas of pinprick hyperalgesia for all of the treatment groups (p=0.03 for the combination, p=0.02 for dextromethorphan, p=0.03 for gabapentin). There was a strong trend in favor of a reduction of allodynia for the combination over placebo (p=0.05), and a significant difference from placebo for gabapentin (p=0.02)

Quality of Life

Both the combination and dextromethorphan alone were significantly better than placebo for the General Health (combination, p=0.01; dextromethorphan, p=0.04) and Physical Health (combination, p=0.001; dextromethorphan, p=0.02) measures, in contrast to gabapentin. The combination, dextromethorphan, and gabapentin were all significantly better than placebo for the Pain domain (combination, p=0.002; dextromethorphan, p=0.001; gabapentin, p=0.03).

Assessment of Blinding

Subjects guessed the identity of the treatment drugs correctly in 27/72 (38%) of the individual treatment periods, a finding of less than chance for the 4 treatments. There was no significant difference in the proportions of patients with moderate or better pain relief who could not correctly guess their treatments.

Choice of Best Treatment

When considering which of the four treatments provided the best pain relief at the completion of the study, 7/18 (38.9%) chose the combination, 6/18 (33.3%) chose dextromethorphan alone, 5/18 (27.8%) chose gabapentin alone, and 2/18 (11.8%) chose placebo as their best treatment (p=0.04). When considering the balance between analgesia and side effects at the completion of the study, 8/18 (47.1%) chose the combination, 3/18 (17.5%) chose dextromethorphan alone, 4/18 (23.5%) chose gabapentin alone, and 2/18 (11.8%) chose placebo as their best treatment (p=0.04).

Adverse Effects

Side effects associated with the dextromethorphan-gabapentin combination occurred at doses that approached the MTD of the individual components. A significantly larger proportion of patients taking the combination (p<0.002) and dextromethorphan alone (p<0.002) experienced cognitive side effects compared to either placebo or gabapentin, including fatigue (combination 35%, dextromethorphan 52%, gabapentin 33%, placebo 15%); confusion (combination 30%, dextromethorphan 33%, gabapentin 22%, placebo 5%); dizziness (combination 45%, dextromethorphan 67%, gabapentin 22%, placebo 20%); somnolence (combination 70%, dextromethorphan 62%, gabapentin 33%, placebo 10%); euphoria (combination 50%, dextromethorphan 24%, gabapentin 6%, placebo 5%); and speech difficulty (combination 25%, dextromethorphan 10%, gabapentin 0%, placebo 0%). A significantly larger proportion of patients taking the combination (p=0.01) and dextromethorphan alone (p=0.01) experienced other side effects compared to placebo, including urinary incontinence (combination 20%, dextromethorphan 5%, gabapentin 11%, placebo 5%) and urinary tract infection (combination 35%, dextromethorphan 38%, gabapentin 22%, placebo 15%).

There were no clinically significant differences in any of the laboratory studies obtained, including a hematology panel (leukocyte count, hemoglobin, platelet count), electrolytes (sodium, potassium, bicarbonate, chloride, blood urea nitrogen, creatinine), and chemistry panel (alkaline phosphatase, transaminases, total bilirubin).

Discussion

Chronic oral administration of dextromethorphan, gabapentin, and the dextromethorphan and gabapentin combination in a fixed 1:5 dose-ratio were all superior to placebo in the treatment of spontaneous pain following SCI. Moreover, when compared to placebo and each component alone during the entire 5-week treatment period, the combination was better than either component alone, with an onset of action as early as the first week of therapy. Moreover, that the combination and the individual components relieved the intensity and spread of pinprick-evoked hyperalgesia, as well as the trend of the combination and dextromethorphan toward significance for touch-evoked allodynia. These data support the chronic oral use of gabapentin and dextromethorphan, and supports the hypothesis that targeting complementary but independent pain mechanisms may be an even more effective strategy than using single-drug regimens in SCI pain.

Because of the heterogeneity of pain mechanisms, combination therapy used in a fixed dose ratio may provide a more robust analgesic effect by acting at different sites without reaching a critical threshold for toxicity at any site. The components would have a dose-ratio based in part on how the various components of pain mechanisms were weighted in the patients. We chose a dose-ratio of 1:5 based on clinical experience and current data (Nelson K A, et al. Neurology 48:1212-1218-(1997); Sang C N, et al. American Pain Society Abstracts, 1997; (Rowbotham M, et al. JAMA. 280(21): 1837-42(1998); Backonja M, et al. JAMA 280(21):1831-6 (1998)) of ceiling doses in peripheral neuropathic pain.

Findings in animal models of SCI and peripheral neuropathic pain demonstrate that blockade of excitatory amino acid transmission with NMDA receptor antagonists relieve allodynia and hyperalgesia (Liu S, et al. Brain Res. 756:160-167 (1997); Bennett A D, et al. Brain Res. 859:72-82(2000); Hao J X, et al. Pain 45:175-185 (1991); and Hao J X, and Xu X J. Pain 66:279-285 (1996)) The most comprehensive pharmacological work in SCI has been in the ischemic rat model (Xu X J, et al Anesth Analg. 74:649-652 (1992) and (Xu X J, et al. J Pharmacol Exp Ther. 267:140-144 (1993)). Of the three candidate NMDA receptor antagonists evaluated in the ischemic SCI model, dextromethorphan was the only NMDA receptor antagonist which preserved motor function (Hao J X, et al. Pain 45:175-185 (1991) and Hao J X and Xu X J. Pain 66:279-285 (1996)). All of the currently available NMDA receptor antagonists with affinity at the phencyclidine site (such as dextromethorphan, ketamine, and amantadine) are limited by dose-related side effects. In the context of epilepsy, Rogawski (Rogawski M A. Trends Pharmacol Sci. 14:325-331 (1993)) proposed that the low-affinity channel-blocking antagonists such as dextromethorphan may be less toxic than the higher affinity NMDA receptor antagonists such as ketamine.

Despite this, dextromethorphan's efficacy in patients with peripheral neuropathic pain is limited by a ceiling analgesic effect, thought to be related to its dose-limiting toxicity (Nelson K A, et al. Neurology 48:1212-1218 (1997); Sang C N, et al. American Pain Society Abstracts, (1997)). However, high doses may be necessary to achieve analgesia, as high concentrations of dextromethorphan in the central nervous system are required for neuroprotection (Steinberg G K, et al. J Neurosurg. 84:860-866 (1996)). Thus, inadequate dosing may have accounted for, in part, the inability of McQuay et al. (McQuay H J, et al. Pain 59:127-133 (1994)) to demonstrate a significant analgesic effect of dextromethorphan alone at 81 mg/day in patients with neuropathic pain. Thus, the addition of a second agent that may reduce excitation via different mechanisms of action may have additive or synergistic therapeutic benefit. Because the doses of dextromethorphan were not significantly different when given alone or in combination with gabapentin, we cannot clearly infer synergism of dextromethorphan and gabapentin from this study. On the other hand, we can infer that there may less than additivity for the side effects of these two drugs.

In addition to the possibility of independent mechanistic effects of the individual study drugs, either dextromethorphan or gabapentin may also be enhancing the analgesic effects of concomitant analgesic medications that subjects were taking, although we were unable to detect such an effect. Prior studies in animal neuropathic pain models and patients with postoperative and chronic pain show that dextromethorphan enhances opioid analgesia (Price D D, et al. J Pain Symptom Manage. 19(1 Suppl):S7-11 (2000) and Caruso F S. J Pain Symptom Manage 19(1 Suppl):S31-6 (2000)).

This study is the first randomized controlled clinical trial clearly demonstrating the analgesic and anti-hyperalgesic efficacy of any treatment for central neuropathic pain following spinal cord injury. In addition, this study has shown that a combination of analgesic compounds selective for at least two distinct mechanisms of action widens the therapeutic ratio, and infer that the combination produces at least additivity for analgesia but not for toxicity. Future studies may assess a potential synergistic relationship between component drugs. The results of this study offer hope of analgesic therapy for the treatment of SCI pain, which to date remains refractory to currently available therapies.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treatment of central neuropathic pain in a human, comprising administering chronically, in a plurality of doses comprising an initial dose and subsequent doses, an analgesic amount of dextromethorphan, which analgesic amount corresponds to an amount within the range of greater than 120 mg/day to about 1200 mg/day, wherein at least one of the subsequent doses is higher than the initial dose.

2. The method according to claim 1, wherein the central neuropathic pain occurs acutely or wherein the central neuropathic pain is chronic.

3. The method according to claim 1, wherein the central neuropathic pain is a result of stroke, multiple sclerosis, or an injury, trauma, lesion, tumor or other disorder of the brain or spinal cord.

4. A method of treatment of central neuropathic pain in a human, comprising administering chronically, in a plurality of doses comprising an initial dose and a subsequent doses, an analgesic amount of a combination of dextromethorphan, which analgesic amount of dextromethorphan corresponds to an amount within the range of greater than 120 mg/day to about 1200 mg/day, wherein at least one of the subsequent doses of dextromethorphan is higher than the original dose, and at least one other pharmacologic agent that acts through a different pharmacologic mechanism.

5. The method according to claim 4, wherein the at least one other pharmacologic agent comprises gabapentin.

6. The method according to claim 4, wherein the at least one other pharmacologic agent consists essentially of gabapentin.

7. The method according to claim 4, wherein the central neuropathic pain results from stroke, multiple sclerosis, or an injury, trauma, lesion, tumor, or other disorder of the brain or spinal cord.

8. The method according to claim 1 wherein the step of administering comprises administering to a human suffering from a stroke, a brain lesion, spinal cord injury, or disorder of the brain or spinal cord.

9. The method according to claim 1 wherein the step of administering comprises administering to a human suffering from trauma to the spinal cord.

10. The method according to claim 1 wherein the step of administering comprises administering to a human suffering from multiple sclerosis.

11. The method according to claim 1, wherein the step of administering comprises administering to a human suffering from a tumor within or surrounding the spinal cord.

12. The method according to claim 1, wherein the step of administering comprises administering to a human suffering from a vascular lesion compressing the spinal cord.

13. The method according to claim 4 wherein the at least one other pharmacologic agent acts at a different site from dextromethorphan.

14. The method according to claim 5, wherein the combination is administered as a fixed 1:5 dose-ratio of dextromethorphan and gabapentin.

15. A method of treatment of central neuropathic pain in a human comprising chronically administering an analgesic composition that consists essentially of dextromethorphan such that an analgesic amount of dextromethorphan within the range of greater than 120 mg/day to about 1200 mg/day is administered, wherein the analgesic composition is administered in a plurality of doses comprising a first dose and subsequent doses, wherein at least one of the subsequent doses is larger than the initial dose.

16. The method according to claim 1, wherein the step of administering comprises administering to a human suffering from a lesion.

* * * * *